United States Patent
Kovi et al.

(10) Patent No.: US 12,215,234 B2
(45) Date of Patent: Feb. 4, 2025

(54) PROCESS FOR THE PURIFICATION OF METHYLENE BLUE

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Hemant Mande, Gujarat (IN); Dusanapudi Naga Venkata Raghavulu, Vadodara (IN)

(73) Assignee: RK Pharma Solutions LLC, Piscataway, NJ (US)

( * ) Notice: Subject to any disclaimer, the term of this patent is extended or adjusted under 35 U.S.C. 154(b) by 34 days.

(21) Appl. No.: 17/023,544

(22) Filed: Sep. 17, 2020

(65) Prior Publication Data

US 2022/0049102 A1 Feb. 17, 2022

(30) Foreign Application Priority Data

Sep. 21, 2019 (IN) .............................. 201921038163

(51) Int. Cl.
*C09B 21/00* (2006.01)
(52) U.S. Cl.
CPC .................................. *C09B 21/00* (2013.01)

(58) Field of Classification Search
CPC ............................ C09B 21/00; C09B 67/0096
See application file for complete search history.

(56) References Cited

U.S. PATENT DOCUMENTS

2016/0251325 A1* 9/2016 Sinclair ................ C07D 279/18
544/36

FOREIGN PATENT DOCUMENTS

WO WO-2020250186 A1 * 12/2020 ........... C07D 279/18

* cited by examiner

*Primary Examiner* — Amanda L. Aguirre
(74) *Attorney, Agent, or Firm* — Nikitas E. Nicolakis; Lombard & Geliebter LLP (57) ABSTRACT

The present application provides method for producing methylene blue that includes the steps of providing a reaction mixture having one or more methylene blue intermediates; precipitating metal from the reaction mixture; and producing therefrom crude methylene blue. The crude may further be purified, resulting in methylene compounds having low impurities, preferably having a purity greater than about 97%, having Azure B impurity no greater than 2.5%, and/or a total metal content no greater than 77 ppm. Formulations containing such compounds are also provided.

2 Claims, 4 Drawing Sheets

PROCESS FOR THE PURIFICATION OF METHYLENE BLUE

BACKGROUND

The present application relates to a process for the preparation of diaminophenothiazinium compounds. The present application particularly relates to Methylene blue of formula I. The present application further relates to a process for the purification of methylene blue to get less metal content in the final compound. A further subject of the present application is the use of such compounds for the preparation of medicaments and their use in treating various diseases.

The diaminophenothiazinium dyes are known. In particular, the medical dye or antidote, methylthioninium chloride (3,7-bis(dimethylamino)phenothiazin-5-ylium chloride), known commonly as "methylene blue", has in relatively recent times extended its use to a number of medical applications beyond its traditional uses. Other common names for this dye include 3,7-bis(dimethylamino) phenazathionium chloride, tetramethylthionine chloride, C.I. 2015, C.I. Solvent Blue, Swiss Blue, C.I. Basic Blue 8, Aniline Violet and Urolene Blue.

Methylene Blue Injection, US Pharmacopeia (USP) is a sterile solution of methylene blue (methylene blue injection) in water for injection suitable for parenteral administration. Methylene blue is available in two dosage form 0.5% solution and 1% solution. 0.5% solution contains 50 mg of methylthioninium chloride (active substance) in 10 ml (5 mg/ml). 1% solution contains 100 mg of methylthioninium chloride (active substance) in 10 ml (10 mg/ml). The molecular formula of methylene blue is $C_{16}H_{18}ClN_3S$ and its molecular weight is 319.85. Methylene blue has the following structural formula:

Formula I

Methylene blue industrial applications have included its use as a colouring agent, redox indicator, dye, an immunological or microbiological stain, in photo electronic imaging, as an environmental metal sequestrant, a leather dye and an antiseptic.

In the clinical field, methylene blue has two primary established uses: firstly, as an antidote for methaemoglobinaemia, and occasionally for cyanide and carbon monoxide poisoning, and, secondly, as a chromodiagnostic or chromoendoscopic agent for a wide variety of clinical conditions, such as examining cellular dysplasia in for example Barret's Oesphagous and endoscopic polypectomy, and Fallopian tube patency and Fistula detection. Methylene blue is capable of forming a complex with non-toxic cyanide or nitrite, to be use as an antidote, and may also be used in the treatment of urinary calculi, obliterans, neurodermatitis and oral ulcers.

Methylene blue was first synthesized in 1876 by German chemist Heinrich Caro in the form of zinc salts. In this instance, methylene blue was synthesized by nitrosylation of dimethylaniline, subsequent reduction to form N,N-dimethyl-1,4-diaminobenzene, and then subsequent oxidative coupling in the presence of hydrogen sulphide ($H_2S$) and iron(III) chloride ($FeCl_3$).

Bernthsen described subsequent studies of methylene blue and methods for its synthesis. Various available routes for the synthesis of methylene blue are summarised below.

Journal of American Chemical Society; 1940, 62(1), 204-211 discusses synthesis of methylene blue using N,N-dimethylaniline as a starting material. The process involves an excess trichloride presence of iron, oxidative addition of hydrogen sulphide and reaction with hydrochloric acid solution to give the crude product methylene blue. The product is recrystallized from water to give the methylene blue product. The method of methylene blue synthesized only 8% yield of the product, the yield is too low so it does not have commercial value.

Another method for the synthesis of methylene blue is discussed in the Journal of Physical Organic Chemistry, 12, 194-200 (1999). The method involves the reaction of phenothiazine with sodium nitrate to give 3,7-dinitro-phenothiazine, which is further reacted with acetic anhydride to give 1-(3,7-dinitro-phenothiazin-10-yl)ethanone. 1-(3,7-dinitro-phenothiazin-10-yl)ethanone is then reduced by using palladium carbon to give 1-(3,7-diamino-phenothiazin-10-yl) ethanone. 1-(3,7-diamino-phenothiazin-10-yl)ethanone is then reacted to give 1-(3,7-bis(dimethylamino)-phenothiazin-10-yl)ethanone. Further reacting 1-(3,7-bis(dimethylamino)-phenothiazin-10-yl)ethanone with ferric chloride and hydrochloric acid it gives methylene blue. Synthesis route is depicted below.

This route produces large amounts of nitric oxide gas and acid-containing wastewater, which is having a very large negative impact on the environment. In the final step, a large amount of ferric chloride is oxidized, the product high in iron content, required multiple washes, a large amount of strongly acidic iron-containing wastewater which is having a greater negative impact on the environment. The article has also reported a yield of the fourth step of 30%. With high raw material cost, this process is not feasible for industrial scale.

PCT Publication No. WO 2005054217, which is incorporate herein by reference, describes methylene blue derivatives and a process for the preparation thereof. The method for preparing these compounds uses phenothiazine as starting product. Currently, all known methods for preparing phenothiazine call for metal reactants of which the metal atoms chelate the phenothiazine at the end of the synthesis. The products obtained by this process are therefore naturally contaminated with metal residues, in addition to the usual organic contaminants, such as azure B.

Another Publication No. WO 2006032879, which is incorporate herein by reference, describes a process for preparing methylene blue which comprises a reduction step with iron, an oxidation step with sodium dichromate, and an oxidation step with copper sulfate.

These processes require tedious and expensive purifications to be carried out in order to reduce the impurities, in particular the metal impurities of methylene blue. Despite the subsequent purification steps, these various processes inevitably produce a methylene blue that includes many metal impurities and also organic impurities, in particular azure B, azure C, and azure A.

WO 2006032879 asserts that it is possible to achieve a level of metal impurities representing 10% of the maximum threshold fixed by the European Pharmacopeia, but, according to the examples, it is noted that this level is not obtained simultaneously for all metals, and the results of the purification steps are not always reproducible. A detailed analysis of the metal contents of various commercially available methylene blues is illustrated in that document.

The use of methylene blue in the medical field are limited because of both metal impurities and of organic impurities, as defined by the current Pharmacopoeias such as European Pharmacopoeia and United States Pharmacopeia.

Marshall and Lewis describe the analysis of metal contaminants in commercial thiazine dyes by atomic absorption spectrophotometry in "Metal contaminants in commercial dyes," Stain Technology, Vol. 50 (3), 1975, pp. 143-147. They report 38 samples with metal concentrations that vary widely between 0.02% and 25.35% of individual samples; the metals examined were iron, potassium, sodium and zinc. They also report that other metals may be present which were not analysed. Aluminium, chromium, manganese, and copper, are all involved in synthetic procedures for methylene blue and are almost certain to be present. Importantly, they report large variations in the metal content of commercial samples of methylene blue.

The purification of methylene blue from metal impurities and from Azure derivatives has no simple resolution due to the sequestering effect of the diaminophenothiazinium structure and to the chemical analogy of organic contaminants. The same applies to the purification of Azure derivatives that are used as dyes in diagnostics.

A process for the synthesis of methylene blue is discussed in the Fundamental Processes of Dye Chemistry (pg. no 311-312) by Fierz-David and Blangley. In this, they describe methods for the synthesis of methylene blue from dimethylaniline as starting material.

In first step (a) Nitrosodimethylaniline is prepared from dimethylaniline by treatment with nitrite in acid solution. The nitroso compound is then reduced to form p-aminodimethylaniline. In step (b) the p-aminodimethylaniline is oxidized in acid solution with another molecule of dimethylaniline, and simultaneously a thiosulfonic acid group is introduced. This step is accomplished by oxidizing in the presence of thiosulfuric acid in statu nascendi. In step (c) the thiosulfonic acid is then oxidized further and undergoes ring closure to form methylene blue.

The detailed process includes in step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline in aqueous acid (HCl) solution using zinc dust solution. In steps (c), (d), and (e), the p-aminodimethylaniline is oxidized in aqueous acid solution with another molecule of dimethylaniline, and simultaneously a thiosulfonic acid group is introduced; the ring is then closed using manganese dioxide or copper sulfate. More specifically, a clear neutral solution of p-aminodimethylaniline is acidified ($H_2SO_4$), and a non-reducing zinc chloride solution is added ($ZnCl_2$ with $Na_2Cr_2O_7$). Aluminium thiosulfate ($Al_2(S_2O_3)_3$) and sodium thiosulfate ($Na_2S_2O_3$) are added. Sodium dichromate ($Na_2Cr_2O_7$) is added. The mixture is heated and aerated. Dimethylaniline and Sodium dichromate ($Na_2Cr_2O_7$) is added. The mixture is heated and becomes dark greenish-blue in colour due to the formation of the thiosulfonic acid of Bindschedler green. Manganese dioxide or copper sulfate is added, and the mixture heated, and the dye precipitates from the concentrated zinc chloride solution.

This process has several drawbacks including low purity, low yield, unstable compound on formulation scale, high number of impurities present in final compound, and more metal content.

Desired pH for the methylene blue formulation as per USP is in between 3.0-4.5. By following the process discussed in the Fundamental Processes of Dye Chemistry, it is found that if methylene blue is isolated in the range of 3.0-4.5 the pH of the formulation containing methylene blue increases above 4.5, which is not acceptable by pharmacopeia standard.

Thus there is a need for a process which gives highly pure methylene blue and meeting all the criteria required by regulatory. The present application overcomes one or more of the drawbacks involved in prior processes, including the process discussed in Fundamental Processes of Dye Chemistry. Drawbacks are overcome by carefully monitoring the reaction, identifying the root cause and solving to the problem to get highly pure compound.

SUMMARY

The present application relates to the preparation of methylene blue preferably having metal content in the lowest possible limits, as well as their use in the treatment and/or prophylaxis of physiological and/or pathophysiological conditions. Formation of impurity is mainly because of the presence of metal presence in final compound. Thus, to achieve the desired purity, the processes discussed herein reduce at least the metal content in final product.

In general, the present application provides purification of methylene blue or a pharmaceutically acceptable salt thereof. The application provides processes which give better purity, stability and/or control in metal content as compare to prior processes. The application also provides solution control of the pH in the formulation of methylene blue.

Figure 4A:
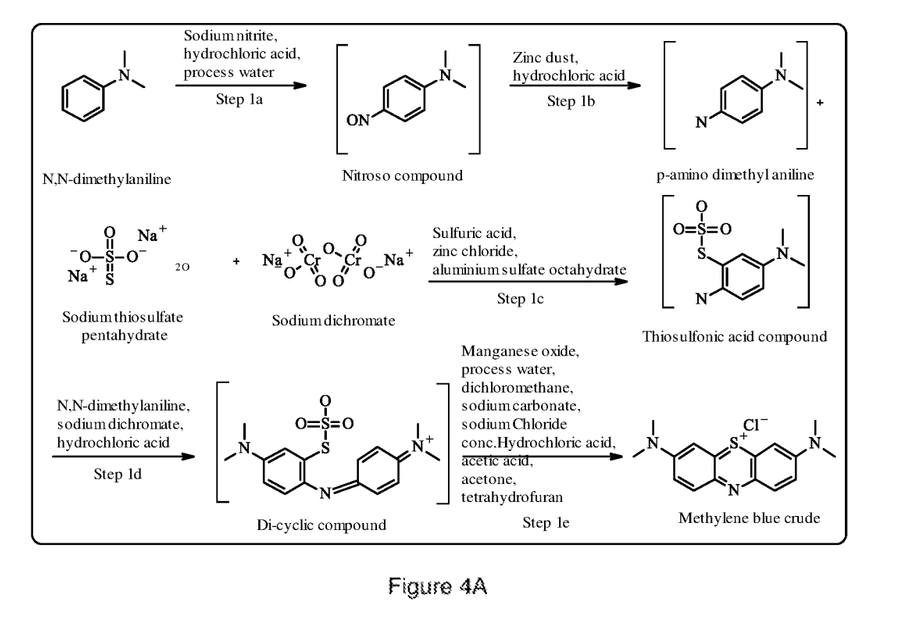
FIGS. 4A-4B illustrate processes for the preparation of methylene blue according to at least one embodiment of the processes disclosed herein.
Figure 4B:
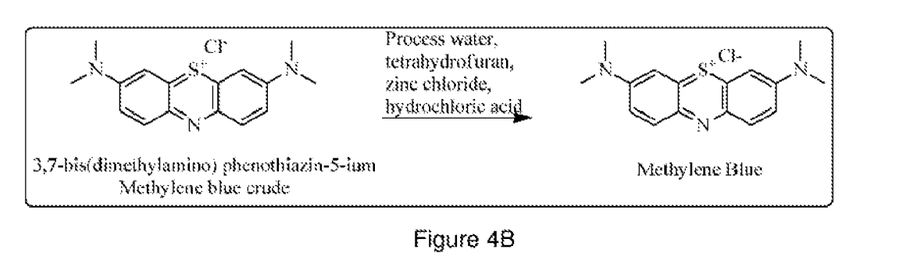

Accordingly, at least one object of this application is to develop the improved process for the purification of methylene blue having less metal content and/or control of impurity in the final compound. A schematic representation of a process for the preparation of methylene blue according to one embodiment of the processes disclosed herein is depicted generally in FIG. 4.

In one aspect, a compound is provided that includes methylene blue having a purity greater than about 97%.

In at least one embodiment, the methylene blue further has Azure B impurity no greater than 2.5%.

In at least one embodiment, the methylene blue further has total metal content no greater than 77 ppm.

In another aspect, a method for producing methylene blue is provided that includes: providing a reaction mixture comprising one or more methylene blue intermediates; precipitating metal from the reaction mixture; and producing therefrom crude methylene blue.

In at least one embodiment, the method further includes extracting a solvent from the reaction mixture, wherein the step of precipitating the metal from the reaction mixture is performed during solvent extraction.

In at least one embodiment, the solvent extraction is performed with the reaction mixture having a pH between about pH 9 and about pH 11.

In at least one embodiment, the methylene blue crude is produced in-situ without isolation of any intermediate(s).

In at least one embodiment, the providing the reaction mixture includes: reacting N,N-dimethylaniline with sodium nitrite in hydrochloric acid to obtain an in-situ nitroso compound; reducing the in-situ nitroso compound in the presence of zinc and hydrochloric acid to get obtain in-situ p-amino dimethyl aniline; reacting the in-situ pamino dimethyl aniline with sulfuric acid and zinc chloride in a presence of sodium thiosulfate pentahydrate, sodium dichromate, and aluminium sulphate octahydrate to obtain an in-situ thiosulfonic acid compound; treating the in-situ thiosulfonic acid compound with another molecule of N,N-dimethylaniline in a presence of sodium dichromate and zinc chloride to yield in-situ Di-cyclic compound; and allowing the in-situ Di-cyclic compound to undergo cyclisation reaction in presence of manganese oxide to yield methylene blue crude.

In at least one embodiment, the method further includes purifying the methylene blue crude to obtain methylene blue having a purity greater than about 97%.

In at least one embodiment, the method further includes purifying the methylene blue crude to obtain methylene blue having Azure B impurity no greater than 2.5%.

In at least one embodiment, the method further includes purifying the methylene blue crude to obtain methylene blue having total metal content no greater than 77 ppm.

In at least one embodiment, the method further includes purifying the methylene blue crude in water and tetrahydrofuran, followed by treatment with hydrochloric acid to get stable methylene blue having a pH in range of 3.0-4.5.

In at least one embodiment, the method further includes adjusting the reaction mixture to a pH of less than about 2.

In at least one embodiment, the method further includes purifying the methylene blue crude using a polar solvent to obtain methylene blue.

In at least one embodiment, the polar solvent includes acetic acid.

In another aspect, a formulation is provided that includes methylene blue prepared according to the method or methods disclosed herein.

In at least one embodiment, the methylene blue in the formulation has a purity greater than about 97%.

In at least one embodiment, the methylene blue in the formulation has Azure B impurity no greater than 2.5%.

In at least one embodiment, the methylene blue in the formulation has a total metal content no greater than 77 ppm.

In at least one embodiment, the concentration of methylene blue in the formulation is from about 1 mg/ml to about 20 mg/ml.

Additional aspects of the present invention will be apparent in view of the description which follows.

For the purposes of illustration, drawings represent preferred embodiments, it being understood, however, that the invention is not limited to the precise embodiments shown therein.

DETAILED DESCRIPTION

Important aspects in the preparation of Methylene blue are quality and production costs of the end product. Owing to regulatory requirements, high quality standards have to be met. Of interest in this context are purity and content of the active compound. Coupled to purity, it is in particular the spectrum of by-products which need to be monitored. Minor components have to be toxicologically qualified and assessed. Accordingly, they are listed in specifications and the maximum occurrence in the product is defined. For reasons of product safety and for the good of the patient, the by-product spectrum and the presence of individual contaminants are kept as low as possible to achieve the desired result.

Referring to FIG. 4A, in a first embodiment, the present application provides an improved process for the preparation of crude methylene blue. The process for the preparation of methylene blue crude according to this embodiment is performed as in-situ without isolation of any intermediate(s). The process for the preparation methylene blue intermediate generally includes the reaction of:

a. N,N-dimethylaniline with sodium nitrite in hydrochloric acid to obtain in-situ nitroso compound.

b. the in-situ nitroso compound is further reduced in the presence of zinc and hydrochloric acid to obtain in-situ p-amino dimethyl aniline.
c. the in-situ p-amino dimethyl aniline is further reacted with sulfuric acid and zinc chloride in presence of sodium thiosulfate pentahydrate, sodium dichromate, and aluminium sulphate octahydrate to obtain in-situ thiosulfonic acid compound.
d. the in-situ thiosulfonic acid compound is further treated with another molecule of N,N-dimethylaniline in presence of sodium dichromate and zinc chloride to yield in-situ Di-cyclic compound.
e. the in-situ Di-cyclic compound then undergoes a cyclisation reaction in presence of manganese oxide to yield methylene blue crude.

Referring to FIG. 4B, in another embodiment the process further involves the purification of methylene blue crude to get methylene blue, preferably having less metal content as compared to known processes. In one embodiment, the process involves a purification of methylene blue crude in water and tetrahydrofuran followed by treatment with hydrochloric acid to get a stable methylene blue having a pH in range of 3.0-4.5, which remains stable in stability study.

Figure 1:
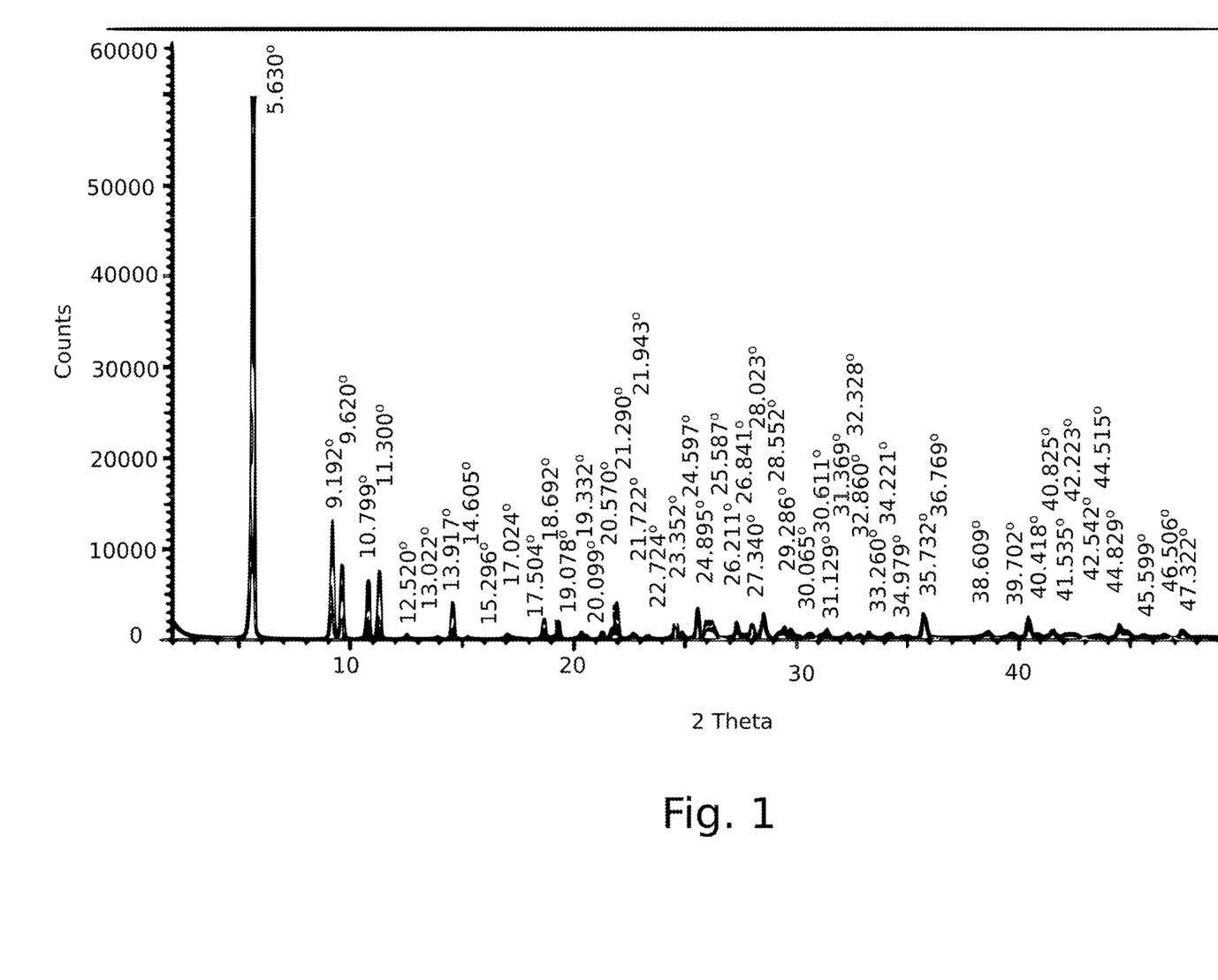
FIG. 1 illustrates a characteristic X-ray powder diffraction pattern of methylene blue form A obtained using the processes disclosed herein.
Figure 2:
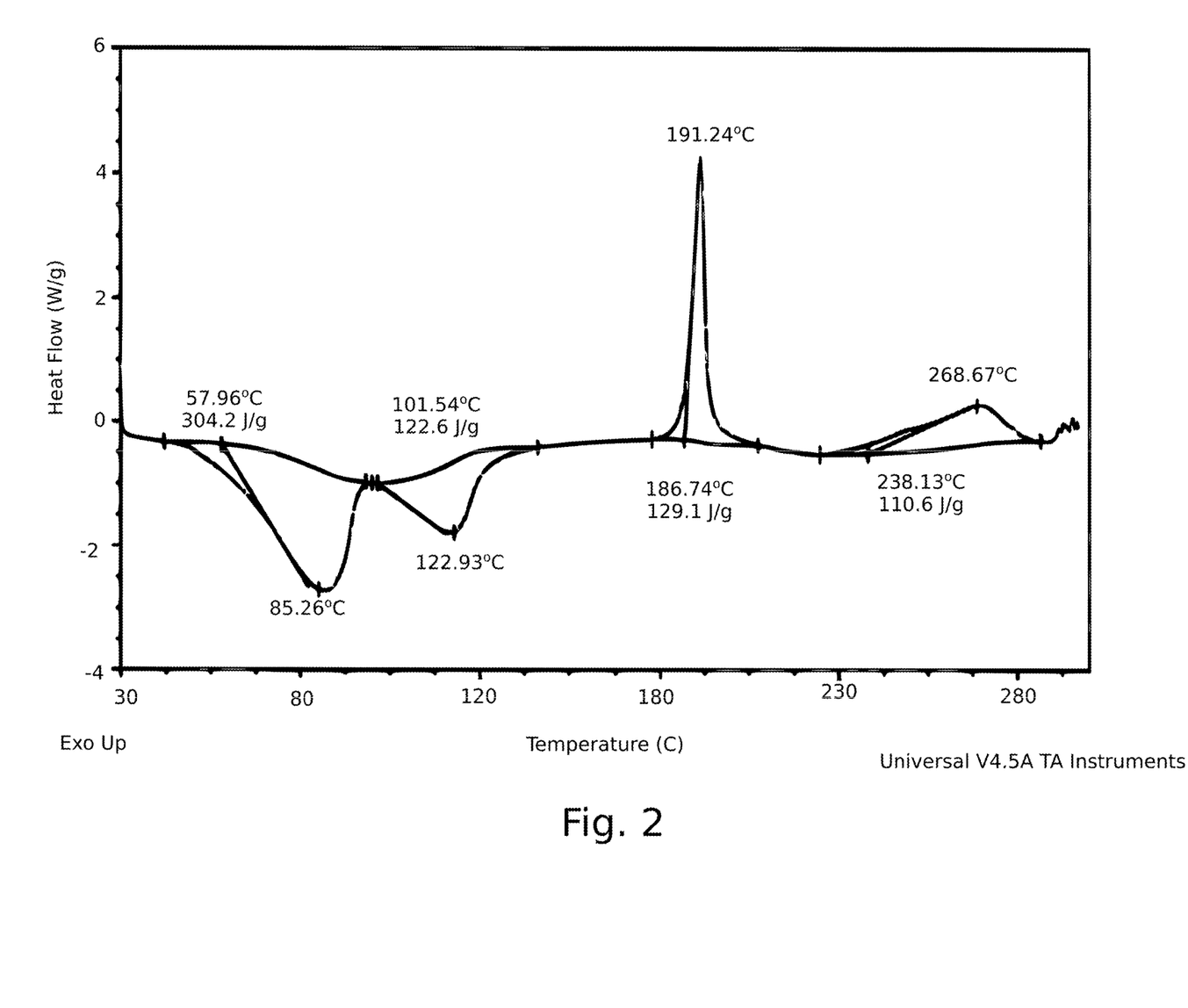
FIG. 2 illustrates a characteristic DSC pattern of methylene blue form A obtained using the processes disclosed herein.
Figure 3:
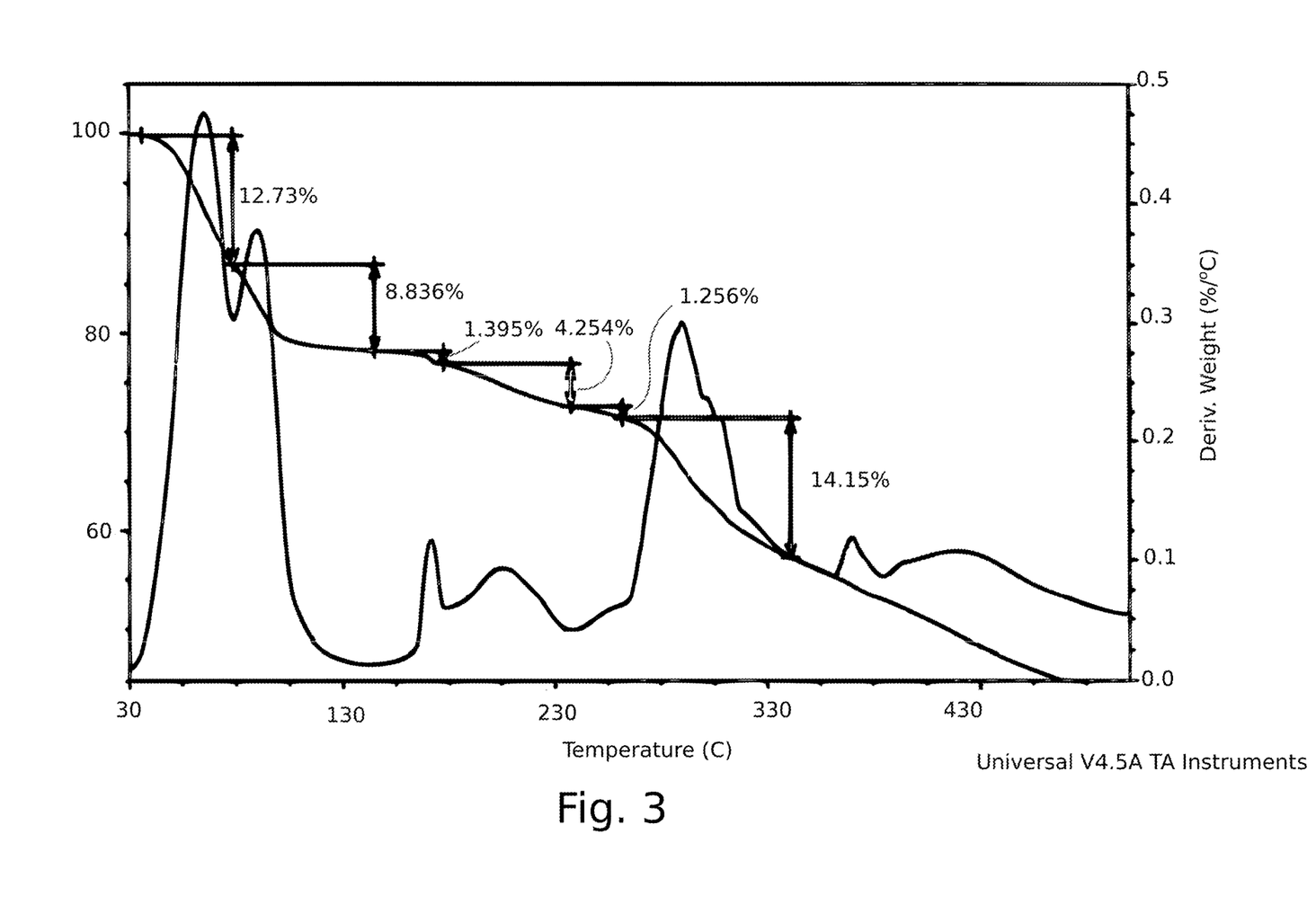
FIG. 3 illustrates a characteristic TGA pattern of methylene blue form A obtained using the processes disclosed herein.

Methylene blue obtained by this process is in crystalline form A. Characterisation details with XRD (x-ray diffraction), DSC (differential scanning calorimetry) and TGA (thermal gravimetric analysis) data for form A is depicted in the drawings (FIGS. 1-3). DSC of crystalline form A is 191.24° C. Methylene blue obtained by this process is pentahydrate.

Four major impurities have been known which are affecting the quality and yield of the methylene blue in the synthesis. These include 1. Azure A, 2. Azure B, 3. Azure C, and 4. Methylene Violet Bernthsen (MVB). The structures for individual impurity are depicted in Table 1.

producing methylene blue which reduces the metal content therein by precipitation during solvent extraction process in the basic condition.

Solvent extraction is done in the basic condition preferably between about pH 9 to about pH 11, more preferably above about pH 10. In a preferred embodiment, extraction is performed by using methylene dichloride at about pH 10.0 to about 10.5. Suitable base(s) required for the adjustment of pH to above about 9 includes but is not limited to sodium carbonate, sodium bicarbonate, potassium carbonate, sodium hydroxide, potassium hydroxide, ammonia, and triethylamine.

Another area of concern is pH of formulated methylene blue. USP mentions that pH of methylene blue formulation should be in between about 3.0 to about 4.5. In formulation, pH of Methylene blue solution tends to increase drastically when the pH of the active pharmaceutical ingredient (API) is kept in between about 3.0 to about 4.5 as per prior art process. To overcome such a problem, the reaction mass pH is preferably kept less than about 2 and more preferably pH of less than about 1. Suitable acids for the adjustment of pH to below about 1 includes, but is not limited to, hydrochloric acid.

Following the process discussed in Fundamental Processes of Dye Chemistry (above) to synthesize methylene blue, one unknown impurity is observed at 0.94 RRT (close to methylene blue peak), as per the USP method, with a range of 0.5% to 1%. The impurity has been isolated and well analysed with mass of 316.1 g/mol. A crystallisation process is provided to reduce the impurity content below about 0.1%. The crude may be purified in polar solvent to remove the impurity at 0.94 RRT. The polar solvent used may be selected from Acetic acid and in the presence of conc HCl. Anti-solvent may be used for the isolation of product. Anti-solvents used may be selected from acetone, acetoni-

TABLE 1

Azure A

Azure B

Azure C methylene violet bernthsen

Formation of an above impurity is observed in the basic condition. Use of inorganic salts in the process for producing methylene blue are the source for the relatively high metal content. Thus, there is an urgent need to develop a process which controls or otherwise limits the metal content in the product, which ultimately improves the purity with minimum genotoxic impurity.

Metal content can be removed by precipitating the metal from the reaction mixture. Prior processes proposed the extraction thereof in acidic condition, which does not give good results. The present application provides a process for trile, THF, DMF, IPA, DIPE or DMSO, or a combination thereof. In a preferred embodiment, acetic acid is used for removal of impurity at 0.94 RRT.

The isolation of crude intermediate may be induced using techniques which include but are not limited to concentrating, cooling, separation, stirring, shaking, combining with an anti-solvent, adding seed crystals, evaporation, flash evaporation, simple evaporation, rotational drying, or the like.

Once the methylene blue is obtained in isolated, drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about, less than about 40° C., less than about 30° C., or any other suitable temperatures; at atmospheric pressure or under a reduced pressure; as long as the crystalline pharmaceutical ingredient is not degraded in its quality. The drying can be carried out for any desired times until the required product quality is achieved. Suitable time for drying can vary from few minutes to several hours for example from about 30 minutes to about 10 or more hours.

Formulation containing methylene blue may then be prepared by using this isolated material. Process for the preparation for methylene blue composition can be selected from any suitable process. Formulation can be either in solid dosage form or liquid dosage form. In a preferred embodiment, liquid dosage form is prepared. The formulation may have a concentration from about 1 mg/ml to about 20 mg/ml or any suitable concentration.

Methylene blue product obtained by this process is then loaded for stability at about 20-25° C. and at about 40° C. Purity and metal content of Methylene blue is tested for up to six months.

Stability data for Methylene blue is depicted in Table 2 & 3

TABLE 2

Stability data at 25° C.

| Trial No. | Trial 1 | Trial 2 | Trial 3 |
|---|---|---|---|
| Profile | 6M 25/60 | 6M 25/60 | 6M 25/60 |
| Purity | 97.54 | 97.6 | 97.56 |
| Azure A | 0.03 | 0.08 | 0.04 |
| Azure B | 2.37 | 2.2 | 2.17 |
| Azure C | ND | 0.01 | ND |
| Highest Unknown | 0.04 | 0.06 | 0.08 |
| Total impurities | 2.46 | 2.4 | 2.44 |
| Metal Content (ppm) | | | |
| Al | 49.1 | 47.57 | 8.31 |
| Cr | 11.68 | 1.79 | 1.76 |
| Cu | 1.91 | 0.74 | 0.7 |
| Mn | 0.68 | 0.61 | 0.48 |
| Zn | 13.14 | 24.89 | 46.16 |
| Total metal content(ppm) | 76.51 | 75.6 | 57.41 |

TABLE 3

Stability data at 40° C.

| Trial No. | Trial 1 | Trial 2 | Trial 3 |
|---|---|---|---|
| Profile | 6M 40/75 | 6M 40/75 | 6M 40/75 |
| Purity | 97.5 | 97.54 | 97.48 |
| Azure A | 0.03 | 0.08 | 0.04 |
| Azure B | 2.41 | 2.26 | 2.26 |
| Azure C | ND | 0.01 | ND |
| Highest Unknown | 0.03 | 0.06 | 0.07 |
| Total impurities | 2.5 | 2.46 | 2.52 |
| Metal Content (ppm) | | | |
| Al | 46.2 | 38.54 | 13.71 |
| Cr | 12.57 | 3.26 | 1.54 |
| Cu | 1.13 | 0.07 | 0.83 |
| Mn | 0.49 | 0.49 | 0.51 |
| Zn | 14.58 | 20.55 | 45.89 |
| Total metal content(ppm) | 74.97 | 62.91 | 62.48 |

The Methylene blue intermediate synthesized by this route has advantageous properties selected from at least one of: chemical purity, stability—such as storage stability, stability to pH, stability to dehydration, stability to polymorphic conversion, flowability, solubility, morphology or crystal habit, low hygroscopicity and low content of residual solvents. In a preferred embodiment, the methylene blue produced has a purity greater than about 97% and Azure B impurity no greater than between 2.0-2.5%.

Certain specific aspects and embodiments of the present application will be explained in more detail with reference to the following examples, which are provided only for purposes of illustration and should not be construed as limiting the scope of the present application in any manner.

Experimental Section

Preparation of Methylene Blue Crude

Step 1a

In a round bottom flask (RBF) water (1.86 lit) was added. The solution was cooled to approximately 5° C. N, N-dimethylaniline (300 g) and HCl (37%)(0.9 lit) was charged into the cooled water. To this mixture was added dropwise an aqueous solution of sodium nitrite (0.18 kg) in water (0.9 lit). The resulting suspension was stirred at a low temperature (0-5° C.) for 4 hours.

Step 1b

Charged hydrochloric acid solution into the above reaction mass at 0 to 5° C. Zinc dust powder (0.70 kg) was added in one aliquot portions. The mixture was stirred for 2 hours at 0 to 5° C. The mixture was filtered through celite bed.

Step 1c

The filtrate ml was collected and cooled to 0 to 5° C. in RBF. Sulfuric acid (27 ml) was added into the reaction mass at 0 to 5° C. Charged zinc chloride solution (30 gm) in (0.3 lit) water at 0 to 5° C. Charged aluminum sulphate solution (0.25 kg) in (0.75 lit) water at 0 to 5° C. Charged sodium thiosulphate solution (0.72 kg) in water (0.6 lit) at 0 to 5° C. Added sodium dichromate solution (0.234 kg) in process water (0.36 lit) into the reaction mass under vigorous stirring at 0 to 5° C. The solution was then stirred at low temperature (at 0 to 5° C.) for 2 hours.

Step 1d

A homogenous solution of N,N-dimethylaniline (0.25 lit), water (0.36 lit) and HCl (0.33 lit) was then added to the chilled reaction mass. Then a solution of sodium dichromate dihydrate (0.45 kg) in water (0.75 lit) was added dropwise at 0 to 5° C. Raise the reaction mass temperature to 25 to 30° C. and stir the reaction mass for 1.0 hr. at 25 to 30° C. Heated the reaction mass up to 70° C. to 75° C.

Step 1e

Charged manganese dioxide solution (0.15 kg) in process water (0.36 lit) into the reaction mass under vigorous stirring at 70° C. to 75° C. Further heat the reaction mass upto 80° C. to 85° C. Stirred the reaction mass for 6.0 hrs at 80° C. to 85° C. A deep blue colour was formed. Cooled the reaction mass to 25° C. to 30° C. Filtered the reaction mass though Buchner funnel and discarded filtrate ml.

Wet cake was taken in RBF and methanol (2×2.4 lit) was added. Reaction mass was filtered. Charged wet cake in RBF and make slurry with water (2×5.1 lit). The filtrate was collected and treated with sodium chloride (1.0 kg). The mixture was stirred until the deep blue colour disappeared. The mixture was then filtered and wash with tetrahydrofuran (300 ml).

Wet cake was charged and dissolved in (10.5 lit) process water and adjusted the reaction mass pH 9.0 to 10.0 with sodium carbonate solution (15%) at 20° C. to 30° C. Stirred the reaction mass for 15 minutes at 25° C. to 30° C. Filtered the reaction mass though celite bed, charged filtrate ml and slowly adjusted the reaction mass pH 3.0 to 7.0 with dil. hydrochloric acid solution at 20° C. to 30° C. Charged sodium chloride (1.0 kg) into the reaction mass under stirring and stir for 10 minutes at 25° C. to 30° C. Filtered and washed with tetrahydrofuran (2×250 ml). Charged process water (18.0 lit) and wet cake into RBF at 25° C. to 30° C. Adjusted the reaction mass pH between 10.00 to 10.50 by using sodium carbonate solution (15%) and washed the aqueous layer with methylene dichloride (5.1 lit) for five times. Took aqueous layer and adjusted pH 2.0 to 4.0 with diluted hydrochloric acid solution at 25° C. to 30° C. and treated with sodium chloride (1.0 kg). The mixture was stirred until the deep blue colour disappeared. The mixture was filtered and wash with tetrahydrofuran (300 ml).

Charged acetic acid (900 ml), wet cake and conc. hydrochloric acid (1050 ml). Slowly charged acetone (3 lit) into the reaction mass. Stirred the reaction mass for 2.0 hrs. at 25° C. to 35° C. Filtered and washed with tetrahydrofuran (2×150 ml). Charged process water (18.0 lit) and wet cake into RBF and stir for 15 minutes at 25 to 30° C. Charged sodium chloride (1.0 kg) in reaction and mixture was stirred until the deep blue colour disappeared. The mixture was filtered and washed with tetrahydrofuran (300 ml).

Charged process water (18.0 lit) and wet cake into RBF at 25° C. to 30° C. Adjust the reaction mass pH between 10.00 to 10.50 by using sodium carbonate solution (15%) and wash the aqueous layer with methylene dichloride (5.1 lit) for five times. Took aqueous layer and adjust pH 2.0 to 4.0 with dilute hydrochloric acid solution at 25° C. to 30° C. and treated with sodium chloride (1.0 kg). The mixture was stirred until the deep blue colour disappeared. The mixture was filtered and wash with tetrahydrofuran (300 ml). Charged wet cake and process water (15 lit) and adjust pH 1.5 to 2.0 with dilute hydrochloric acid solution at 25° C. to 30° C. and treated with sodium chloride (1.0 kg). The mixture was stirred until the deep blue colour disappeared. The mixture was filtered and washed with tetrahydrofuran (2×250 ml). Dried the material in vacuum at 40° C. to 45° C. to obtain Dry wt.=153 gm and Yield: 37.87%.

Preparation of Methylene Blue:

Step 2

Stage-I (methylene blue crude, 150 gm) was taken in methanol (1.5 Lit) and reaction mass was stirred at 25° C. to 35° C. to get homogeneous solution. Reaction mass was filtered through 0.45μ, and then filtrate mL cooled to get 0° C. to 5° C. Conc. hydrochloric acid (150 mL) was slowly added into the reaction mass at 0° C. to 5° C. Reaction mass was stirred for 10 to 20 minutes at 0° C. to 5° C. Fine filtered Tetrahydrofuran (1.5 lit) was added into reaction mass and stirred for 30 minutes at 0° C. to 5° C. Reaction mass was filtered and washed with fine filtered Tetrahydrofuran (300 mL). Wet cake was taken in fine filtered process water (750 ml) and stirred for 30 minutes at 25° C. to 30° C. Fine filtered tetrahydrofuran (1.5 lit) was charged into reaction mass at 25° C. to 30° C. Reaction mass stirred for 1.0 hr. at 25° C. to 30° C. Reaction mass was filtered and washed with fine filtered Tetrahydrofuran (2×150 mL). Material was dried in vacuum oven at 30° C. to 35° C. for 2.0 hrs.

Wet cake was added in solution containing azure-B (3.0 gm), process water (1.8 lit), zinc chloride (825 mg) and tetrahydrofuran (3.6 lit) into RBF at 25° C. to 30° C. Reaction mass heated to get 63° C. to 68° C. and stirred for 1.0 hr at 63° C. to 68° C. Reaction mass cooled to 25° C. to 35° C. and maintained for 12.0 hrs. at 25° C. to 30°. Conc. hydrochloric acid (600 mL) was slowly added into the reaction mass at 25° C. to 35° C. and stirred for 3.0 hrs. at 25° C. to 35° C. Reaction mass filtered and washed with fine filtered tetrahydrofuran (300 ml). Material was dried in vacuum oven (with 200 mbar Vacuum) at 30° C. to 35° C. for 2.0 hrs. to obtain Dry wt.=135 gm. and Yield: 90%.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A method for producing methylene blue comprising:
   a) providing a reaction mixture comprising one or more methylene blue intermediates;
   b) reducing the metal content therein by precipitation during solvent extraction under basic conditions wherein the basic condition is between about pH 9 and about pH 11; to form a reaction mass;
   c) producing crude methylene blue by further adjusting the pH of the reaction mass to an acidic pH with acid;
   d) purifying the crude methylene blue by treatment with polar solvent to remove the impurity at 0.94 RRT;
   e) producing methylene blue having purity greater than about 97% by repeating steps (b) and (c) followed by purification using water and THF; wherein, providing the reaction mixture comprises,
   I. reacting N,N-dimethylaniline

N,N-dimethylaniline
with sodium nitrite in hydrochloric acid to obtain an in-situ nitroso compound;

nitroso compound
II. reducing the in-situ nitroso compound nitroso compound
in the presence of zinc and hydrochloric acid to obtain in-situ p-amino-N,N-dimethyl aniline;

p-amino-N,N-dimethyl aniline

III. reacting the in-situ p-amino-N,N-dimethyl aniline p-amino-N,N-dimethyl aniline
with sulfuric acid and zinc chloride in the presence of sodium thiosulfate pentahydrate, sodium dichromate, and aluminium sulphate octahydrate to obtain an in-situ thiosulfonic acid compound;

thiosulfonic acid compound

IV. treating the in-situ thiosulfonic acid compound thiosulfonic acid compound with another molecule of N,N-dimethylaniline in the presence of sodium dichromate and zinc chloride to yield an in-situ di-cyclic compound;

Di-cyclic compound and

V. allowing the in-situ di-cyclic compound

Di-cyclic compound to undergo a cyclisation reaction in the presence of manganese oxide to yield methylene blue crude;

Methylene blue crude.

2. The method of claim 1, comprising purifying the methylene blue crude using a polar solvent comprising acetic acid to obtain methylene blue.

* * * * *